(12) United States Patent  
Tang et al.

(10) Patent No.: US 7,704,753 B2  
(45) Date of Patent: *Apr. 27, 2010

(54) DEVICES AND METHODS FOR ANALYTE ASSAYS WITH BUILT-IN RESULT REPORTING USING RECOGNIZABLE SYMBOLS

(75) Inventors: Zuifen Tang, HangZhou (CN); Dengfeng Xiong, Hangzhou (CN); Shujiang Wu, HangZhou (CN); Zhumin Guan, Hangzhou (CN)

(73) Assignee: Inverness Medical Switzerland GmbH, Zug (CH)

( * ) Notice: Subject to any disclaimer, the term of this patent is extended or adjusted under 35 U.S.C. 154(b) by 438 days.

This patent is subject to a terminal disclaimer.

(21) Appl. No.: 11/073,028

(22) Filed: Mar. 3, 2005

(65) Prior Publication Data

US 2006/0199277 A1    Sep. 7, 2006

(51) Int. Cl.  
    *G01N 33/543* (2006.01)
(52) U.S. Cl. .................. 436/514; 436/170; 436/518; 436/169; 436/172; 436/175; 436/530; 436/807; 436/823; 435/287.7; 435/287.9; 435/805; 422/57; 422/58; 422/59; 422/60
(58) Field of Classification Search ................ 436/514, 436/418, 169, 172, 175, 530, 533, 807, 170, 436/823, 518; 435/287.8, 287.9, 805, 57, 435/58, 59, 60; 422/57, 58, 59, 60  
See application file for complete search history.

(56) References Cited

U.S. PATENT DOCUMENTS

| | | | |
|---|---|---|---|
| 4,916,056 A | * | 4/1990 | Brown et al. ............. 435/7.92 |
| 5,008,080 A | * | 4/1991 | Brown et al. ............. 422/56 |
| 5,075,078 A | | 12/1991 | Osikowicz |
| 5,130,290 A | | 7/1992 | Tanimoto |
| 5,160,701 A | * | 11/1992 | Brown et al. ............. 422/56 |

(Continued)

FOREIGN PATENT DOCUMENTS

CN          1340707          3/2002

(Continued)

OTHER PUBLICATIONS

Delphion INPADOC Record for CN1511711, 2004.

*Primary Examiner*—Bao-Thuy L Nguyen  
(74) *Attorney, Agent, or Firm*—DLA Piper LLP (US)

(57) ABSTRACT

The present invention provides devices, methods and kits for detecting the presence of an analyte in a liquid sample and indicating to the user the presence or absence of the analyte through the formation of a recognizable symbol during the assay. In one embodiment, the present invention provides test strips having a matrix including a sample application zone, a reagent zone, and a detection zone. Within the detection zone are located positive and negative control areas, and an analyte binding area. The positive control area contains one or more components that exhibit a first color when dry and a second color when wetted. When the assay is conducted, the positive control area is wetted by the assay fluids and turns to a second color, thereby functioning as a positive procedural control. When analyte is present in the sample, it binds at the analyte binding area, which interacts with the positive control area to form a second recognizable symbol at the detection zone.

18 Claims, 6 Drawing Sheets

U.S. PATENT DOCUMENTS

| | | | |
|---|---|---|---|
| 5,656,503 A * | 8/1997 | May et al. | 436/514 |
| 6,194,224 B1 | 2/2001 | Good et al. | |
| 6,680,205 B1 | 1/2004 | Elhard | |
| 6,689,619 B2 | 2/2004 | Elhard | |
| 6,855,561 B2 | 2/2005 | Jerome | |
| 2003/0157699 A1 | 8/2003 | Jerome | |
| 2003/0211634 A1 | 11/2003 | Jerome | |

FOREIGN PATENT DOCUMENTS

| | | | |
|---|---|---|---|
| CN | 1465977 | | 1/2004 |
| CN | 1511711 | | 7/2004 |
| WO | WO 88/08534 | * | 11/1988 |
| WO | WO 94/01775 | | 1/1994 |
| WO | WO 97/31268 | * | 8/1997 |
| WO | WO2004/003559 | | 1/2004 |

* cited by examiner

DEVICES AND METHODS FOR ANALYTE ASSAYS WITH BUILT-IN RESULT REPORTING USING RECOGNIZABLE SYMBOLS

FIELD OF THE INVENTION

The present invention is directed to devices for the detection of an analyte and the presentation of test results in as recognizable symbols.

BACKGROUND OF THE INVENTION

The following Background of the Invention is intended to aid the reader in understanding the invention and is not admitted to be prior art.

The inclusion of positive and negative control tests in the performance of an assay is considered an important component of any assay. In immunological tests, these control tests are often performed by including an analyte binding control test in the assay, which may appear as a colored line on the test strip. These types of control tests are effective for verifying that the assay device is functioning correctly, but they also result in added expense in making the device and performing the assay, particularly when the specific binding molecules used in the control test are produced as a result of elaborate procedures. Additionally, these types of controls can be confusing for the untrained general consumer and lead to improper test interpretation. There is therefore a need for better methods and apparatuses for performing sample collection and testing.

SUMMARY OF THE INVENTION

The present invention provides devices, methods and kits for detecting the presence of an analyte in a liquid sample and indicating to the user the presence or absence of the analyte using recognizable symbols. In one embodiment, the present invention provides test strips having a matrix, including a sample application zone, a reagent zone and a detection zone. Within the detection zone are located positive and negative control areas, and an analyte binding area. The positive control area contains one or more components that exhibit a first color when dry and a second color when wetted. The analyte binding area contains binding molecules that capture an analyte, which can be a labeled analyte. The analyte binding area and positive control area interact with each other to form a recognizable symbol and thereby provide the test result. In one embodiment, the positive control area is present on the matrix in the shape of a minus sign, and the one or more components are selected so that the positive control area will change from white to red upon exposure to an aqueous solution. In this embodiment, the assay begins with a dry test strip and the positive control area and the test strip are both white in color. Therefore, before sample is applied, the positive control area is not apparent upon observation of the detection zone. When liquid sample is applied, it flows through the matrix and through the detection zone, thereby wetting the positive control area as it passes through, and thus causing the positive control area to turn from white to red. Therefore, a minus sign becomes visible in the detection zone. If no analyte is present in the sample, only the minus sign is visible in the detection zone and a negative test result is communicated to the user. However, if analyte is present in the sample, the labeled analyte is captured in the analyte binding area and the labeled analyte accumulates and provides a color, and the analyte binding area interacts with the minus sign (the positive control area) to form a plus sign, thus communicating a positive test result to the user. The symbols selected can be any recognizable symbols, for example, a plus sign, a minus sign, an "X" or another symbol known in the art or in general parlance as conveying a particular meaning. The invention also provides methods of using the devices, and kits containing the devices.

In a first aspect the present invention provides a device for detecting the presence or absence of an analyte in a sample. The device has a matrix that supports the flow of a liquid sample, an application zone on the matrix for receiving a liquid sample, a detection zone on the matrix having a positive control area that has one or more components that exhibit(s) a first color when dry and a second color when wet. The detection zone also has an analyte binding area that has a specific binding molecule. The device also has one or more reagent zones having reagents for conducting the assay.

In one embodiment, the one or more components include a colorless or pale-colored basic dye. The matrix can be a nitrocellulose assay strip, and the positive control area can be in the shape of a minus sign situated on the assay strip. The analyte binding area can be composed of two areas situated on either side of the positive control area and having a specific binding molecule that binds to the analyte or to a molecule bound to the analyte. The two areas are aligned so that the positive control area and analyte binding area interact to form a recognizable symbol when the positive control area is wet and analyte is present in the sample. The recognizable symbol can be a plus sign or any recognizable symbol. Many examples of colorless or pale-colored basic dyes are described in U.S. Pat. No. 5,130,290.

In another embodiment, the positive control area further contains a positive control filament, and the one or more components are part of an aqua-chromic dye contained on the filament. "Aqua-chromic" means that a color change occurs upon exposure to an aqueous solution. The specific binding molecule can be an antibody or antibody fragment, and the one or more components contain a basic dye. In one embodiment, the analyte is human chorionic gonadotropin (hCG). The positive control area can be demarcated by one or more positive control filaments present in the detection zone, and the positive control area does not contain a member of a specific binding pair.

In another embodiment, the analyte binding area further contains a specific binding molecule that specifically binds to the analyte and has a label that provides a detectable signal. The label can be a colored particle, such as a dextran bead. The analyte binding area can be present as a bar situated latitudinally along the axis of the strip, and further contain a specific binding molecule for the analyte or for a molecule bound to the analyte. The positive control area can be composed of two areas situated at either side of the analyte binding area, and the positive control area and analyte binding area interact to form a recognizable symbol.

In another aspect, the present invention provides methods of determining the presence or absence of an analyte in a liquid sample. The method involves placing the liquid sample onto a device as described herein, allowing the liquid sample to flow through the matrix and thereby pass through the one or more reagent zones so that reagents for conducting the assay react with the liquid sample to form a detectable reaction product when analyte is present in the liquid sample. The liquid sample is allowed to flow through the detection zone thereby wetting the material that exhibits a first color when dry and a second color when wet. Analyte contained in the sample is retained on the analyte binding area as sample flows through the detection zone. The detection zone of the device is observed to determine the presence or absence of analyte in the liquid sample.

In one embodiment, the one or more components are contained on a positive control filament. The positive control area can contain a positive control filament containing the one or more components, and the positive control filament is wetted as liquid sample passes through the detection zone, thereby causing the one or more components to exhibit the second color. The analyte binding area can be present in the shape of a bar situated latitudinally along the axis of the strip and contain a specific binding molecule for the analyte bound to a label.

In another embodiment the matrix is a test strip made of a bibulous material, the positive control area is present in the shape of a minus sign situated longitudinally along the axis of the bibulous material, and the analyte binding area includes two areas situated on either side of the positive control area, and the analyte binding area and positive control area interact to form a recognizable symbol. The analyte binding area can be present in the shape of a bar situated latitudinally along the axis of the strip, and the analyte binding area can be a specific binding molecule for the analyte bound to a label.

In further embodiments, analyte present in the sample is labeled with a detectable label as it passes through the reagent zone, and labeled analyte is retained at the analyte binding area as sample passes through the detection zone.

In another aspect, present invention provides kits for determining the presence or absence of an analyte in a fluid. The kits contain a device of the present invention, as described herein, and instructions for use of the device. The test device of the kit can be configured to test for the presence of hCG in a sample, and the instructions explain how to use the device to test for the presence of hCG in urine. In other embodiment, the device can be configured to test for the presence of luteinizing hormone (LH) or follicle stimulating hormone (FSH) in a biological fluid, and the instruction provided in the kit describe how to use the device to test for the presence of these substances.

The summary of the invention described above is not limiting and other features and advantages of the invention will be apparent from the following detailed description, as well as from the claims.

DETAILED DESCRIPTION

In the following detailed description, reference is made to the accompanying drawings that form a part hereof, and in which is shown by way of illustration specific embodiments in which the invention may be practiced. It is understood that other embodiments may be utilized and structural changes may be made without departing from the scope of the present invention.

Test Devices

Figure 1A:
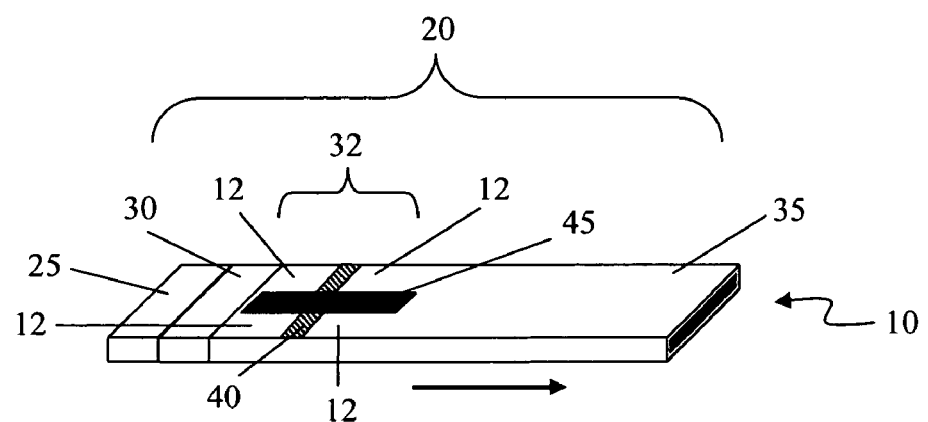
FIG. 1A provides a perspective view of one embodiment of the device of the present invention, having a matrix 20. The matrix includes a sample application zone 25, a reagent zone 30, and a detection zone 32. The detection zone contains a positive control area 45 present in the shape of a minus sign. In this embodiment the positive control area 45 has been printed or painted on the nitrocellulose 35. The detection zone also contains an analyte detection area 40 and a negative control area 12. An arrow indicates the direction of sample flow.

In one embodiment the devices of the invention utilize test strips to detect the presence of an analyte in a liquid sample. The devices convey the test results to the user with recognizable symbols that are formed by the interaction of visible signals from the positive control area and the analyte binding area. FIG. 1A illustrates one embodiment of the present device 10, a test strip having a matrix 20 that supports the flow of a liquid sample. The matrix includes a sample application zone 25 where liquid sample is applied to the device, a reagent zone 30 and a detection zone 32. The reagent zone 30 contains reagents for conducting the assay, and more than one reagent zone can be present on the test strip, depending on the requirements of the particular assay being conducted. The detection zone 32 includes a positive control area 45, an analyte binding area 40, and a negative control area 12. The negative control zone is an area where color should not form if the assay is functioning correctly. In this embodiment the negative control zone 12 is conveniently designated by those areas surrounding the plus sign that forms when analyte is present in the sample (i.e., when a plus sign is selected as the recognizable symbol).

Figure 1B:
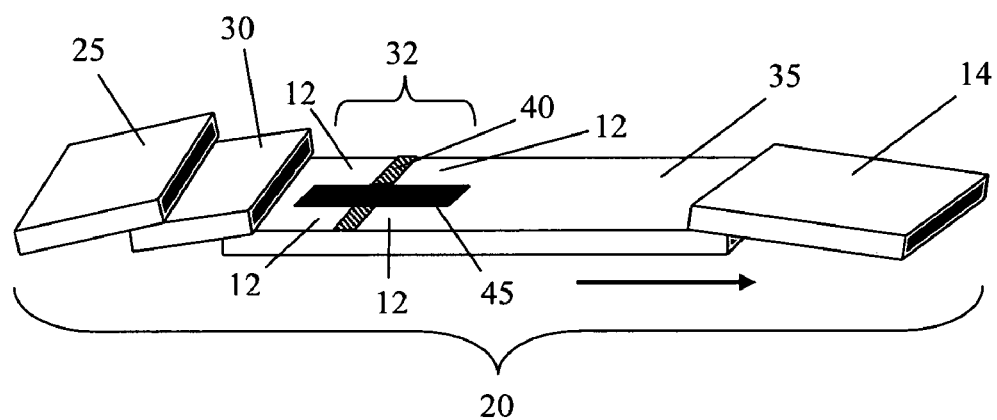
FIG. 1B provides a perspective view of another embodiment of the present invention. In this embodiment, the matrix 20 is composed of multiple materials, which are in fluid communication with each other. The positive control area 45 is present in the shape of a minus sign, and is striped, printed, coated, or painted on the nitrocellulose.

FIG. 1B illustrates another embodiment of the invention. In this embodiment, the matrix 20 is composed of multiple overlapping materials, including a sample application pad 25, a reagent pad 30, a nitrocellulose strip 35 and an absorbent pad 14. The detection zone 32 is located on the nitrocellulose strip. The positive control area and negative control area are located within the detection zone. The absorbent pad provides an absorbent sink to absorb liquid sample and therefore promote liquid flow through the matrix until the conclusion of the assay. In various embodiments, the matrix components can be supported by one or more adhesive backings (not shown).

Figure 4A:
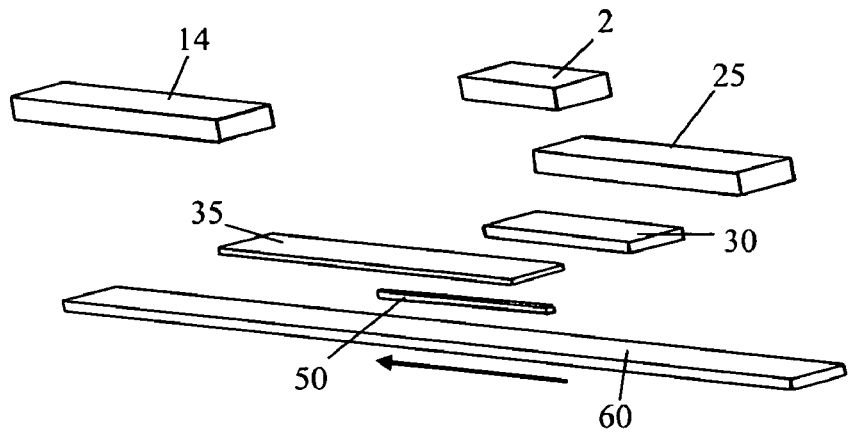
FIG. 4A provides an exploded view of yet another embodiment of the present device. In this embodiment, the filament 50 is present in the matrix below the nitrocellulose 35, and the test strip includes a bottom support 60. The filament 50 is in liquid communication with the reagent pad 30. In certain embodiments, a cover pad 2 may be used to promote contact between the sample pad, reagent pad and nitrocellulose underlying the cover pad.

In another embodiment of the device (FIG. 4a), the positive control filament 50 is treated with a water-sensitive ink and positioned between a nitrocellulose strip 35 and a backing 60. In this embodiment the filament 50 is made of a bibulous paper, which has been impregnated with a water-sensitive reagent. The filament 50 is placed across the axis of the analyte binding area so that, in the event of a positive result, the positive control area interacts with the analyte binding area to form a plus sign. In this embodiment, one side of the filament 50 is underneath the nitrocellulose strip 35 and the other side of the filament is in liquid communication with the reagent pad 30 or the sample application pad 25. A "positive control filament" refers to a structure of the device that contains the one or more components that provide a first color when dry, and a second color when wetted. The filament need not take any particular shape, but will usually be in the shape of an elongated member on the device visible in the detection zone. The shape of the filament will depend on the recognizable symbol(s) used in the assay. The filament can be present as an extension of another structure of the device, and can also be present as an independent structure on the device.

Figure 4B:
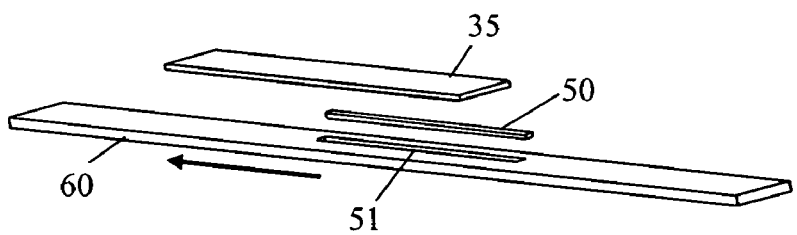
FIG. 4B illustrates an embodiment of the invention with a groove 51 cut into the bottom support 60. The filament 50 is placed into the groove and nitrocellulose 35 is situated on top of the groove.

In another embodiment (FIG. 4b) the filament is placed into a groove 51 cut into the backing 60, and also lies across the axis of the analyte binding areas, so that a plus sign forms when analyte is present in the sample.

Figure 5A:
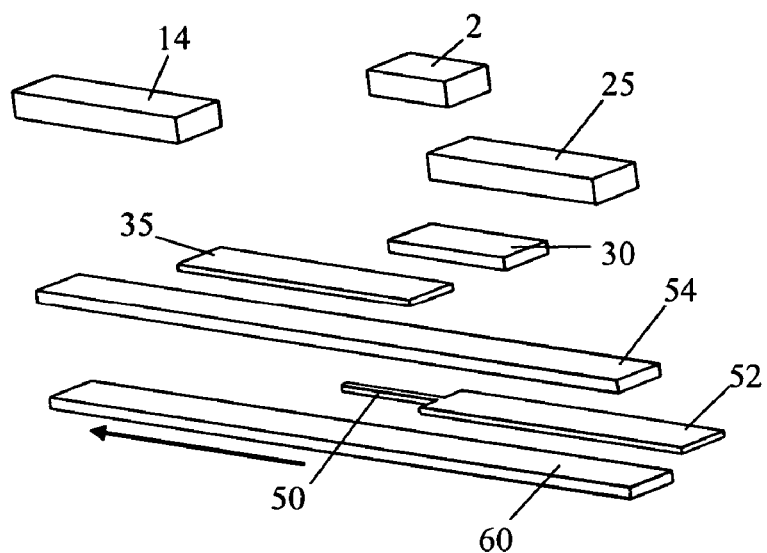
FIG. 5A is an exploded view of yet another embodiment of the present device. In this embodiment, the filament 50 projects from a positive control pad 52 and is present under the nitrocellulose 35. In this embodiment a clear support layer 54 is present between the positive control pad 52 and filament 50, and the nitrocellulose 35.
Figure 5B:
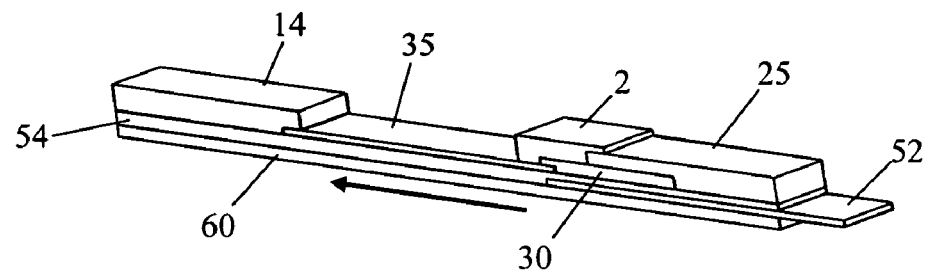
FIG. 5B provides an assembled perspective view of the device shown in FIG. 5A.

In another embodiment (FIG. 5) the positive control filament 50 is present as an extension of a positive control pad 52. The filament 50 extends underneath the nitrocellulose and crosses the axis of the analyte binding areas 40, to form the plus sign when analyte is present in the sample and the minus sign when no analyte is present in the sample. In this embodiment the filament 50 is impregnated with the color-changing reagent, and the filament 50 and positive control pad 52 are in fluid communication with each other and with the reagent zone 30 and sample application zone 25. Therefore, when fluid sample is applied to the sample application zone 25, the positive control pad 52 and filament 50 become wet, thereby causing the color-changing reaction to occur. The filament 50 interacts with the analyte binding area to form the recognizable symbol.

Figure 6A:
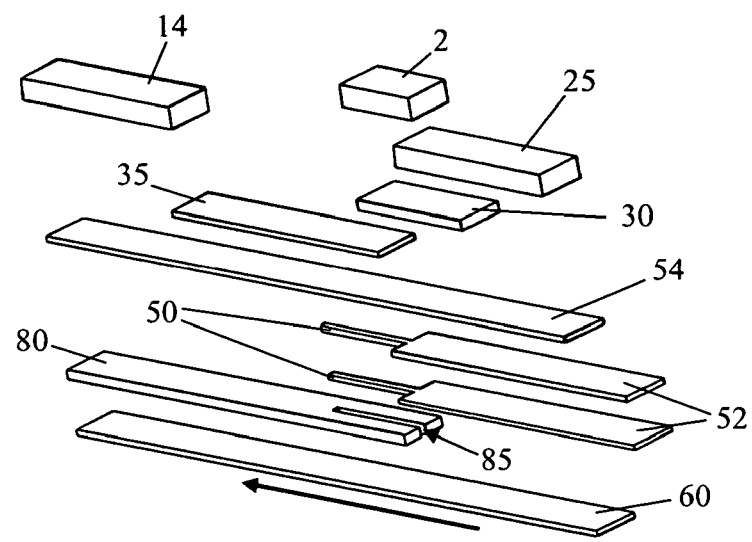
FIG. 6A is an exploded view of a further embodiment of the present device, having two positive control pads 52 and two filaments 50. Additionally, there is a support 80 with a groove 85 sized and shaped to support the two filaments 50.
Figure 6B:
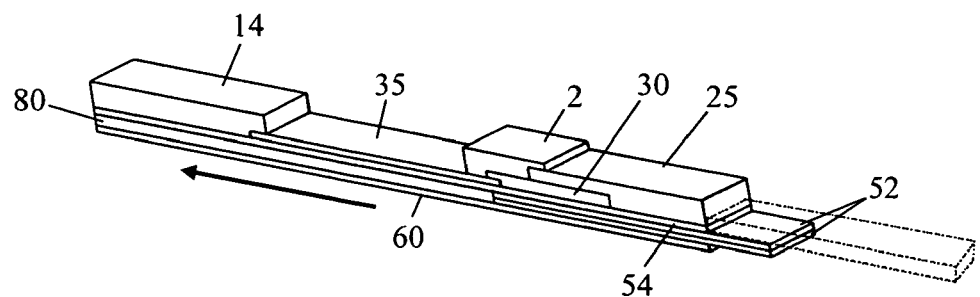
FIG. 6B provides an assembled perspective view of the device shown in FIG. 6A. An optional sample collection pad is shown as dashed lines.

In the embodiment depicted in FIG. 6, the device contains an additional support layer 80 to support the filament 50. The filament 50 is inserted into a groove 85 cut in the support layer 80. The backing 60 can be attached (e.g., by adhesive) to the support layer 80.

The devices of the invention can be provided in the form of a test device, featuring a test strip and a holder for holding the test strip. The holder can be a hollow plastic body with windows located to allow viewing of the detection zone and access to the sample application zone. In another format the devices are provided as a test strip, and no holder is included. The holder can also be located only at one end of the test strip to enable a user to pick it up without contamination of the device, and the sample application zone placed into a sample solution.

In some formats the devices can also include a control line, in addition to the positive control area. In these formats the control line can appear upstream or downstream of the positive control area. A positive result is determined not only by viewing the detection zone for the presence of a recognizable symbol, but also by comparing the analyte binding area to the control line. In some assays the relative intensities of the two lines are compared to determine a positive or negative result for the assay. In one format of this embodiment the analyte is luteinizing hormone.

Matrix

In one embodiment the test strip contains a bibulous material providing a matrix to support the flow of liquid. "Matrix" refers to a material that supports the flow and transport of fluid. In one embodiment the matrix is a bibulous material. The flow of fluid through the device can be by force of capillary action. In different embodiments the matrix can be a strip of a single material (FIG. 1A) or the matrix may be assembled from multiple bibulous materials that are in fluid communication with each other (FIGS. 1B-6). "Bibulous" materials are those that readily absorb liquid and through which liquid is transported by capillary action. Examples of bibulous materials include nitrocellulose, filter paper, glass fibers, polyester, and other suitable materials.

Sample Application Zone

The sample application zone can contain a buffer for solubilizing the sample, or can be simply a location on the matrix for the application of sample, but it also can contain other reagents for conducting the assay. For example, "scavenger" antibodies can be present in the sample application zone, the reagent zone, or other zones of the matrix in those embodiments where they are useful. The sample application zone can therefore also be a reagent zone. Sample is advantageously applied in a liquid form to begin the assay, but can also be dried on the test strip and the assay begun by applying water, buffer, or other reagents to solublize the sample and begin the assay. The sample itself can be a liquid sample or a solid sample that has been liquefied or otherwise prepared in a liquid form.

Reagents

The reagents contained in the reagent zone can be movably present in the reagent zone. Some reagents can be attached to a label and bind to analytes of interest present in the sample, thereby providing a labeled analyte. The sample application zone and/or reagent zone can also contain buffers for solubilizing the sample or adjusting the pH, as may be required in the specific assay. In one embodiment the reagent zone contains a specific binding molecule (e.g., an antibody or antibody fragment) linked to a label. The label can be any convenient label, such as a gold sol, a fluorescent dye, or a water soluble dye. The specific binding molecule can bind specifically to one or more epitopes on the analyte of interest, thereby labeling the analyte.

Detection Zone

The detection zone of the device contains the positive control area, negative control area, and the analyte binding area. The negative control area is that space located in the detection zone that is not a part of either the positive control area or analyte binding area. If a detectable signal is detected in this area, the assay is invalid due to a failed negative control. In some embodiments the detection zone is a rectangle or square on a bibulous matrix that encompasses the length of the positive control area or analyte binding areas, measuring longitudinally along a test strip, and is further encompassed by lines drawn perpendicular to the sides of the test strip. The detection zone can also have a plastic part of the device placed over it to provide a viewing window limited within the detection zone. The "detection zone" refers to a view of the device. Thus, structures can be contained in the detection zone whether they are physically located on, in, or under the matrix, as long as they are visible upon observation of the detection zone in either a wet or dry state, or as the result of a positive or negative analyte assay result.

Positive Control Area

The positive control area can be delineated by one or more areas on the device that contain one or more color-changing components that exhibit a first color when dry and a second color when wet. The positive control area can be present as a bar situated longitudinally along the axis of the strip. The bar can be delineated by a material containing the color-changing components. In another embodiment the color-changing components can be affixed to the matrix or backing or other support, to delineate the positive control area. For example, the color-changing components can be attached to a substance that is affixed to the matrix or backing or other support, and can also be affixed directly to these structures. In one embodiment the color-changing components can be attached to a protein, which is itself attached to the nitrocellulose portion of the matrix.

Figure 2A:
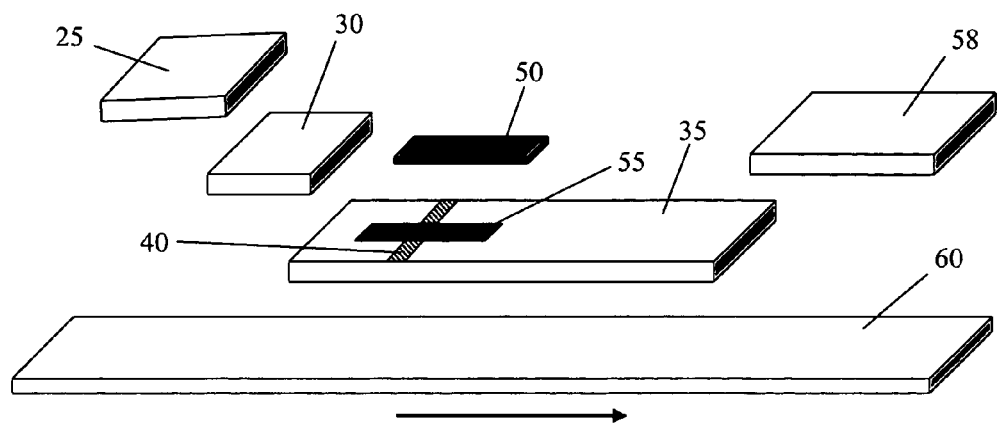
FIG. 2A is an exploded view of another embodiment of the present invention, in which the positive control area comprises a filament 50. The one or more components that provide a first color when dry and a second color when wet are contained on or in the filament. In this embodiment, the filament fits within a groove 55 cut in the nitrocellulose.

In certain embodiments, the positive control area is delineated by a positive control filament. The filament can be made of any suitable material that can retain the color changing components, so that they can exhibit a second color when wet. In some examples the filament is made of paper or another fibrous or cellulosic material that can carry fluid. The filament can be situated to be a part of the matrix, since it will carry fluid. FIG. 2A shows a matrix composed of multiple bibulous materials. The matrix is supported by a backing 60, which in one embodiment contains an adhesive. The adhesive helps to hold the parts of the matrix together and thereby retain fluid communication between the parts. A variety of adhesives can be conveniently used, such as medical grade glue or adhesive strips and double-sided tape. In the embodiment illustrated in FIG. 2A, a nitrocellulose strip 35 is located on top of the backing 60. In different embodiments the nitrocellulose strip 35 can be supported by its own backing (e.g., MYLAR®) or can be placed on the backing 60 containing adhesive, without a separate backing. In this embodiment, the matrix also has a reagent pad 30, a sample application pad 25 and an absorbent pad 58. The components of the matrix abut and slightly overlap each other so that applied sample flows continuously from the application pad to the absorbent pad. The detection zone contains the analyte binding area 40 and a positive control filament 50. The filament contains the one or more components that exhibit a first color when dry and a second color when wetted. The one or more components can be an ink or dye. In this embodiment a groove 55 sized and shaped to fit the filament, is cut in the nitrocellulose. This groove 55 may be cut in the nitrocellulose. Alternatively, a groove can be cut through the backing of the nitrocellulose, if present. During construction of the test strip, the filament is placed in the groove in the nitrocellulose. The reagents can be applied to the analyte binding area of the nitrocellulose either before or after cutting the groove or placing the filament in the groove.

Figure 2B:
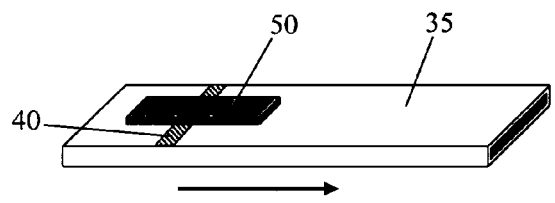
FIG. 2B illustrates an embodiment related to that shown in FIG. 2A. In this embodiment, the positive control area comprises a filament 50 situated on top of the nitrocellulose. The one or more components are contained on or in the filament.
Figure 2C:
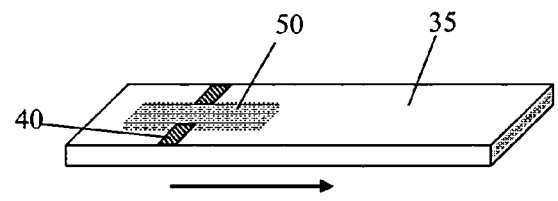
FIG. 2C illustrates an embodiment similar to that shown in FIG. 2B, except that the filament 50 is present underneath the nitrocellulose. When wet, the filament (exhibiting the second color) is visible in the detection zone.

FIGS. 2B and 2C show related embodiments. In the embodiment illustrated in FIG. 2B, the filament is placed on top of the nitrocellulose, instead of in a groove cut into the nitrocellulose. In the embodiment illustrated in FIG. 2C, the filament is placed below the nitrocellulose layer. The filament can be located between the nitrocellulose and the backing of the nitrocellulose (if present), or can also be located between the nitrocellulose and an adhesive backing (when the nitrocellulose does not have its own backing). When wet, the nitrocellulose is translucent or transparent, such that the wetted colored filament 50 is easily visible through the nitrocellulose.

FIGS. 3-6 illustrate more embodiments of the device, in which the filament is present in the shape of a positive control filament 50 protruding from a positive control pad 52. Referring to FIG. 3A, the filament 50 fits into a groove 85 in a support layer 80 (e.g., a plastic strip). The positive control filament 50 can contain a dye containing one or more components that exhibit a first color when dry, and a second color when wetted. The nitrocellulose can be positioned on a support layer 80 and positive control pad 52, such that when the positive control pad 52 becomes wet with sample, the fluid sample flows to the positive control filament 50, causing it to change from the first color to the second color. In one embodiment, when a color-changing dye containing the one or more components is used, it can be formulated to change from white (first color) to red (second color). When the filament turns to the second color, it becomes visible through the overlaying nitrocellulose, which has also been wet by the sample. A backing on the nitrocellulose (e.g., MYLAR®) and/or a transparent support 54 (FIGS. 5 & 6) can be used to prevent sample migration out of the filament.

Various bibulous materials can be used as the positive control filament and/or positive control pad (when utilized), which can be constructed of the same material. Any material that has the ability to transport liquid can be used. The liquid can move through the material by force of capillary action. In one embodiment the positive control pad or positive control filament is a polyamide fiber. Membrane thicknesses of between 0.6 and 1.0 mm are useful, but other thicknesses can be used as convenient. The material is absorptive in its nature, and in this embodiment a polyamide fiber material of 60 mm×10 mm will absorb 0.6 grams of fluid, +/−0.15 grams. Useful polyamide fibers are available as wicking material from Filtrona Fibertec™ (Colonial Heights, Va.). Of course other bibulous materials can also be useful in the invention. For example, surface active media that are often used as filtering materials and utilize either amine or carboxyl groups on the surface of the fiber as substrates for a wide variety of linking agents can also be used. This material also functions well in the present invention as bibulous material when supplied as a sheet or strip, and is also available from Filtrona Fibertec™ (Colonial Heights, Va.). Other embodiments include, but are not limited to, the use of cotton fiber. Polyester is another material that is useful as a bibulous material and is advantageously treated according to methods known in the art with detergents, proteins, and buffers.

Symbols

Recognizable symbols are created by the interaction of the positive control and analyte binding areas on the device. The positive control area can be delineated by choosing a portion of a symbol that will interact with the analyte binding area, and affixing the shape to form the positive control area. The symbol can also be selected to present one recognizable symbol for a negative result, and another recognizable symbol for a positive result, where the positive control area and analyte binding area interact to form a recognizable symbol in the event of a positive assay result. The positive control area contains one or more components that exhibit a first color when dry and a second color when wetted. The symbol (or portion of a symbol) can be affixed to form the positive control area by printing or painting the symbol onto the matrix (and attaching the one or more components that exhibit a first color when dry and a second color when wet to the material to be affixed), or by other methods known in the art. The symbol can be formed above, below, or within the nitrocellulose, or located between the nitrocellulose and a backing for the nitrocellulose.

In various embodiments the "recognizable symbol" can be a plus sign, a minus sign, a dash, a bar, an "X," or another symbol known in the art or in general parlance as conveying a particular meaning that can be associated with the assay result. Any meaningful symbol can be selected, such as a letter from the Roman alphabet, a number, a mathematical operator, a scientific symbol, or a letter from another language or alphabet system, for example a letter from the Chinese, Japanese, or Arabic alphabets. For example, a minus sign is advantageously used to indicate a negative result, because it is a meaningful and easily recognized symbol, and can also be conveniently configured to interact with an analyte binding area to form a plus sign. Other symbols, such an "X," "O," null sign, "Y," "N," "Z," or an arrow, can also be selected. These symbols can be easily read and understood by an untrained user. When the one or more components that change color and the demarcation of the positive control area are selected to be the same color, the recognizable symbol is formed by the interaction of the positive control area and the analyte binding area when a positive result is obtained. When the symbol is a minus sign, it can have either square or rounded edges.

Figure 4C:
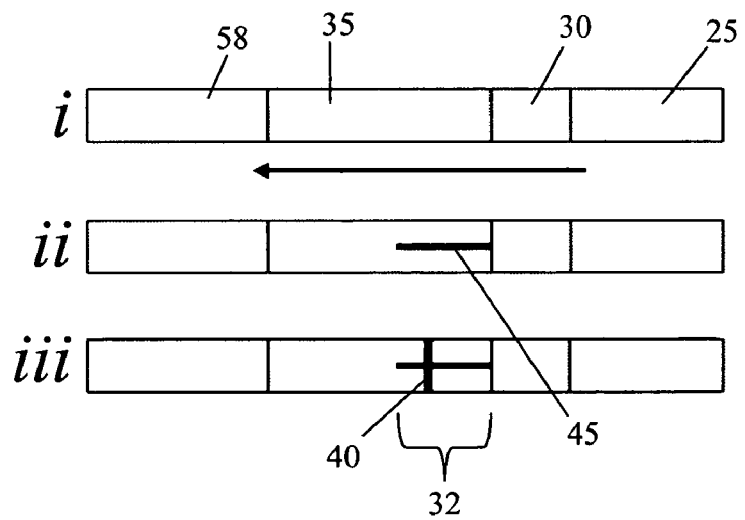
FIG. 4C illustrates the appearance of the test results before use (FIG. 4C i), when the test results are negative (FIG. 4Cii) and when the test results are positive (FIG. 4C iii).

FIG. 4C, i-iii illustrate an embodiment where the recognizable symbol is a plus sign and a minus sign, indicating a positive and negative assay result, respectively. As shown in FIG. 4Ci, prior to use no symbol can be seen in the detection zone 32. If no analyte is present in the sample a minus sign appears in the positive control zone 45, indicating a negative result (FIG. 4Cii). When analyte is present in the sample a plus sign appears through the interaction of the positive control zone and the analyte detection zone 40 (see FIG. 4Ciii), indicating a positive result.

Color-Changing Material

Numerous color-changing components are described in U.S. Pat. No. 5,130,290 to Tanimoto, which is herein incorporated by reference in its entirety, including all tables, figures, and claims. In one embodiment, these components are combined to form an ink or other water sensitive coloring layer that can be applied to a substrate (e.g., a paper or portion of an assay device). In some embodiments, the color-changing components include a colorless or pale-colored basic dye, a color developing material that forms a color on contact with the dye, a desensitizer, and a binder. A wide variety of dyes, color developing materials, desensitizers, and binders may be combined in various ratios to produce an ink with the desired color changing capabilities, and many examples of suitable components and combinations of components are described in U.S. Pat. No. 5,130,290. The one or more components can be formulated as a water sensitive ink. The ink or other water sensitive layer material can also be purchased from Kanzaki Paper Manufacturing Co., Ltd., Tokyo, Japan, Beijing Chuang-Xin Cheng-Ye Tech. Ltd., AD: #02-4-2, Yungang South Lane, Fengtai District, Beijing, China, or Shenzhen Huiju Tech. Ltd., Shenzhen, China. Examples of colorless or pale-colored basic dyes include triarylmethane-based dyes, diphenylmethane-based dyes, thazine-based dyes, lactam-based dyes, and fluoran-based dyes. Examples of color developing materials include 4-tert-butylphenol, alpha-naphthol, beta-naphthol, 4-acetylphenol. Examples of desensitizers include polyethyleneimines, polyoefin glycols, anionic surfactants, and nonionic surfactants. Examples of binders include starches, hydroxyethyl cellulose, methyl cellulose, ethyl cellulose, carboxymethyl cellulose, gelatincasein, gum arabic, and water-soluble polymers. Additional examples of each are found at U.S. Pat. No. 5,130,290.

In one embodiment, the one or more components of the ink produce a white color when dry, and a red color when wet. In other embodiments, an orange or blue color is produced when the material is wetted, but the materials can be selected so that many colors can be formed as desired. The white or colorless ink can be striped onto, coated, printed, or otherwise applied in the detection zone of the device or to the positive control filament. When a positive control filament is used, prior to use it may not be visible to the user, since it is the same color as the matrix, and can also be present within or underneath the nitrocellulose, or in another layer of the fluid-carrying matrix. When the sample flows through the positive control area, the one or more components of the ink are wetted and become red, making the positive control area visible in the shape of a minus sign. In other embodiments, the first color of the positive control area can be a color other than white, and the device changes from a first color to a second color. Any colors desired and for which components are available can be selected as the first and second colors.

Analyte Binding Area

The analyte binding area is positioned on the matrix so that it interacts with the positive control area to provide a recognizable symbol when the analyte of interest is present in the liquid sample. Labeled reagents present in a reagent zone can bind (directly or indirectly) to the analyte of interest, thereby labeling the analyte of interest with a detectable label as it flows through the matrix. The analyte binding area can also contain reagents that bind to a moiety associated with the analyte. That moiety can be an immunological epitope on the analyte itself, or on a reagent bound to the analyte (e.g., a reagent that bound to the analyte as it passed through the reagent zone). In various embodiments the reagent bound to the analyte can be an antibody, a fragment or portion of an antibody, an antibody (or fragment thereof) derived from a species different from the antibody affixed to the analyte binding area, or another member of a specific binding pair, for example, avidin, streptavidin, or biotin, which itself can be bound to a moiety bound to the analyte.

In one embodiment the analyte binding area can be two areas situated on either side of the positive control zone so that when analyte is present in the sample, it is labeled during the assay and is retained at the analyte binding area, and forms the recognizable symbol for a positive assay by interacting with the positive control area. In another embodiment, the analyte binding area is a bar situated latitudinally along the axis of the strip, and contains a specific binding molecule for the analyte, or for a molecule bound to the analyte. In either case, when labeled analyte is present in the sample as it moves through the detection zone, it accumulates at the analyte binding area to provide a detectable color in the analyte binding area. The interaction between the color at the analyte binding area and the positive control area provides the recognizable symbol. In some embodiments the label is a colored particle, which may be a dextran bead, gold sol, or other labeling particle, but the label can be any suitable label that provides a detectable signal.

Reagent Zone

The label that binds the analyte of interest serves to provide the visually detectable signal in the analyte binding area, which will interact with the positive control area to form the recognizable symbol when analyte is present in the sample. Specific binding molecules for the analyte carrying a label can be present in the reagent zone. When the specific binding molecules capture the analyte, and when the labeled analyte is bound within the analyte binding area, the area becomes visible due to the accumulation of the label in the area. A "specific binding molecule" for the analyte refers to a binding molecule that binds to the analyte and does not substantially bind to any other molecule present in the sample. The specific binding molecule for the analyte can also bind to a molecule that correlates with or indicates the presence of analyte in the sample. By substantial binding is meant that binding occurs to an extent that will change or obscure the result of the assay. In some embodiments the specific binding molecule can be an antibody or an antibody fragment (e.g., the Fab region of an antibody), an antigen, a receptor or fragment of a receptor that binds a ligand, or a member of a biotin-streptavidin pair or other type of binding pair.

A label can thus be provided in the reagent zone, and as the sample flows through the reagent zone the analyte is bound with a label that provides a detectable signal. A "label pad" is an area of the matrix where there is present a label for the analyte suspected of being present in the sample. Therefore, a reagent zone can be a label pad. The "label" can be any suitable label that provides a detectable signal. For example, the label can be a sol particle, a fluorescent molecule, a chemiluminescent molecule, a metal or alloy (e.g. colloidal gold), or a sac, in particular a liposome containing a visible dye. Also useful are hydrophobic sols, which hydrophobic organic dyes or pigments are insoluble in water or soluble only to a very limited extent. The label can also be polymer particles, such as colored polystyrene particles (e.g., spherically shaped). Other useful particulate labels include ferritin, phycoerythrins or other phycobili-proteins, precipitated or insoluble metals or alloys, fungal, algal, or bacterial pigments or derivatives such as bacterial chlorophylls, or other plant materials. In certain embodiments, the label is a colored particle, such as a dextran bead. In other embodiments, the label and the dye used for the positive control are selected to have similar colors, to enhance the interaction of the two signals in producing a single apparent symbol on or in the matrix.

In other embodiments, the label can be a labeled specific binding molecule (e.g., an antibody) for the analyte. For example, in one embodiment the analyte of interest is human chorionic gonadotropin (hCG), and the label that attaches to the hCG is gold-sol labeled anti-hCG antibody. When the sample reaches the reagent zone (or label pad), the hCG present in the sample is bound by the gold-anti-hCG antibody. The labeled antibody does not interfere with the binding of capture molecule present in the analyte binding area, which binds the labeled hCG. For example, the label can bind one portion of the analyte and the capture molecule can bind another portion of the analyte, or can bind the label. The hCG-anti-hCG antibody-gold complex migrates downstream in the matrix. When the complex reaches the analyte binding area the capture molecule binds to form a complex of gold-anti-hCG antibody-hCG-anti-hCG antibody. The capture molecule can be another specific binding molecule for hCG, or a specific binding molecule for a moiety bound to the hCG analyte. When the gold-anti-hCG specific binding molecule-hCG-anti-hCG specific binding molecule complex is bound to the analyte binding area, the analyte binding area is colored by the gold label on the complex and therein becomes visible to the unaided eye. In one embodiment the specific binding molecules are antibodies or antibody fragments. The labeling and capture binding molecules can bind to different epitopes on the analyte. In one embodiment the labeled specific binding molecule binds to beta-hCG, and the capture binding molecule binds to alpha-hCG.

"Antibody" refers to an immunoglobulin, whether natural or partially or wholly synthetically produced. The term also includes derivatives thereof which maintain specific binding ability. The term also covers any protein having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, IgG, and IgE. An "antibody fragment" is any derivative or portion of an antibody which is less than full-length. The antibody fragment can retain at least a significant portion of the full-length antibody's specific binding ability. Examples of antibody fragments include, but are not limited to, Fab, Fab', F(ab')$_2$, scFv, Fv, dsFv diabody, and Fd fragments.

The antibody fragment may be produced by any means. For instance, the antibody fragment may be enzymatically or chemically produced by fragmentation of an intact antibody or it may be recombinantly produced from a gene encoding the partial antibody sequence. Alternatively, the antibody fragment may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

Single-chain Fvs (scFvs) are recombinant antibody fragments consisting of only the variable light chain ($V_L$) and variable heavy chain ($V_H$) covalently connected to one another by a polypeptide linker. Either $V_L$ or $V_H$ may be the NH$_2$-terminal domain. The polypeptide linker may be of variable length and composition so long as the two variable domains are bridged without serious steric interference. Typically, the linkers are comprised primarily of stretches of glycine and serine residues with some glutamic acid or lysine residues interspersed for solubility. "Diabodies" are dimeric scFvs. The components of diabodies typically have shorter peptide linkers than most scFvs and they show a preference for associating as dimers.

An "Fv" fragment consists of one $V_H$ and one $V_L$ domain held together by noncovalent interactions. The term "dsFv" is used herein to refer to an Fv with an engineered intermolecular disulfide bond to stabilize the $V_H$-$V_L$ pair. A "F(ab')$_2$" fragment is an antibody fragment essentially equivalent to that obtained from immunoglobulins (typically IgG) by digestion with an enzyme pepsin at pH 4.0-4.5. The fragment may be recombinantly produced. A "Fab'" fragment is an antibody fragment essentially equivalent to that obtained by reduction of the disulfide bridge or bridges joining the two heavy chain pieces in the F(ab')$_2$ fragment. The Fab' fragment may be recombinantly produced. A "Fab" fragment is an antibody fragment essentially equivalent to that obtained by digestion of immunoglobulins (typically IgG) with the enzyme papain. The Fab fragment may be recombinantly produced. The heavy chain segment of the Fab fragment is the Fd piece.

Prior to use of the device the analyte binding area may not be apparent to the user. In certain embodiments, the test result will be displayed as a plus sign or a minus sign, depending upon the presence or absence of analyte in the sample. When no analyte is present in the sample, the positive control area becomes visible as a minus sign, since the one or more components will change from a first color to a second color (e.g., from white to red). If analyte is present in the sample, the analyte reacts with the labeled reagent in the reagent zone and is captured in the analyte binding area by the specific binding molecules. In one embodiment the analyte binding area is two areas situated latitudinally on the assay strip on either side of the positive control area. By "latitudinal" is meant perpendicular to the direction of fluid flow through the device, which is usually also perpendicular to the length of the test strip. The positive control area and the analyte binding area interact with each other to produce a recognizable symbol. In one embodiment, the positive control area and analyte binding area interact to display a plus sign, but the analyte binding area can also be arranged with the positive control area to form other recognizable symbols.

In another embodiment, the analyte binding area is present as a single area present latitudinally across the test strip, and the positive control area is present as two areas situated on either side of the analyte binding area. The positive control area is thus present longitudinally on the test strip in two areas, and the analyte binding area is present either on top of the positive control area, or in between the positive control areas. In different embodiments these areas may or may not overlap. The one or more components used in the positive control area or filament can be selected to be of the same or similar colors, so that the positive control area and the analyte binding area will form a single symbol when they interact. Thus, the positive test symbol appears as a plus sign, and a negative test result produces a minus sign.

In yet another embodiment, a plus sign is formed by the positive control area and the analyte detection zone, which may or may not overlap. In this embodiment the analyte binding area is applied to the test strip before the positive control area is applied, providing a plus sign in the event of a positive result, and a minus sign in the event of a negative result.

In a further embodiment the positive control can be placed laterally on the test strip, and the analyte binding area placed longitudinally. In this orientation, the symbol for a positive result would still be a plus sign and a negative test result symbol would be a minus sign, simply oriented differently than in other embodiments.

In related embodiments, the positive control area is composed of multiple, aligned bars (instead of a single bar) that are perpendicular to and abut the analyte detection zone, and thus form a plus sign. Alternatively, the analyte binding area can be composed of multiple, aligned bars that are perpendicular to and abut the positive control area, which together form a plus sign.

In another embodiment, the test and positive control areas interact to form an "X." In this embodiment, the test and positive control areas are placed at an angle to the direction of sample flow. In a further embodiment, the test and positive control areas are arranged so that they interact to form a "Y."

Type of Analytes

The analyte being assayed for presence or absence using the present invention can be any analyte. Examples of analytes that can be readily tested for using the present invention include (but are not limited to) human chorionic gonadotropin (hCG), luteinizing hormone (LH), follicle stimulating hormone (FSH), hepatitis C virus (HCV), hepatitis B virus, hepatitis B surface antigen, HIV, and any drug of abuse. Also, analyte can be detected in any liquid or liquefied sample such as, for example, urine, saliva, oral fluid, blood, plasma, or serum. Additional examples of analytes to be tested for include but are not limited to creatinine, bilirubin, nitrite, protein (nonspecific), blood, leukocytes, sugar, heavy metals or toxins, bacterial components (e.g. proteins or sugars specific to a particular type of bacteria, such as *E. coli*O157:H7, *S. aureus, Salmonella, C. perfringens, Campylobacter, L. monocytogenes, V. parahaemolyticus,* or *B. cereus*). Any other analyte that can be adapted to a lateral flow test format may also be incorporated into the present device.

Types of Samples

Any sample type can be tested with the device of the present invention, including liquids of biological origin (e.g., urine and other body fluids, and clinical samples). Liquid samples may be derived from solid or semi-solid samples, including feces, biological tissue, and food samples. Such solid or semi-solid samples can be converted into a liquid sample by any suitable method, for example by mixing, chopping, macerating, incubating, dissolving or enzymatically digesting solid samples in a suitable liquid (e.g., water, phosphate-buffered saline, or other buffers). "Biological samples" include samples derived from living animals, plants, and food, including for example urine, saliva, blood and blood components, cerebrospinal fluid, vaginal swabs, semen, feces, sweat, exudates, tissue, organs, tumors, tissue and organ culture, cell cultures and conditioned media therefrom, whether from humans or animals. Food samples include samples from processed food components or final products, meat, cheese, wine, milk and drinking water. Plant samples include those derived from any plant, plant tissue, plant cell cultures and conditioned media therefrom. "Environmental samples" are those derived from the environment (e.g., a water sample from a lake or other body of water, effluent samples, soil samples, ground water, ocean water, and runoff water. Sewage and related wastes can also be included as environmental samples.

Methods of Use

The present invention also provides methods of using the devices of the invention to detect the presence or absence of an analyte in a liquid sample. The methods can include the steps of placing a liquid sample onto the sample application zone of a device of the present invention, and allowing the liquid sample to flow through the test strip. The liquid sample can be placed on the sample application zone by any convenient means, for example by using a dropper.

Figure 3A:
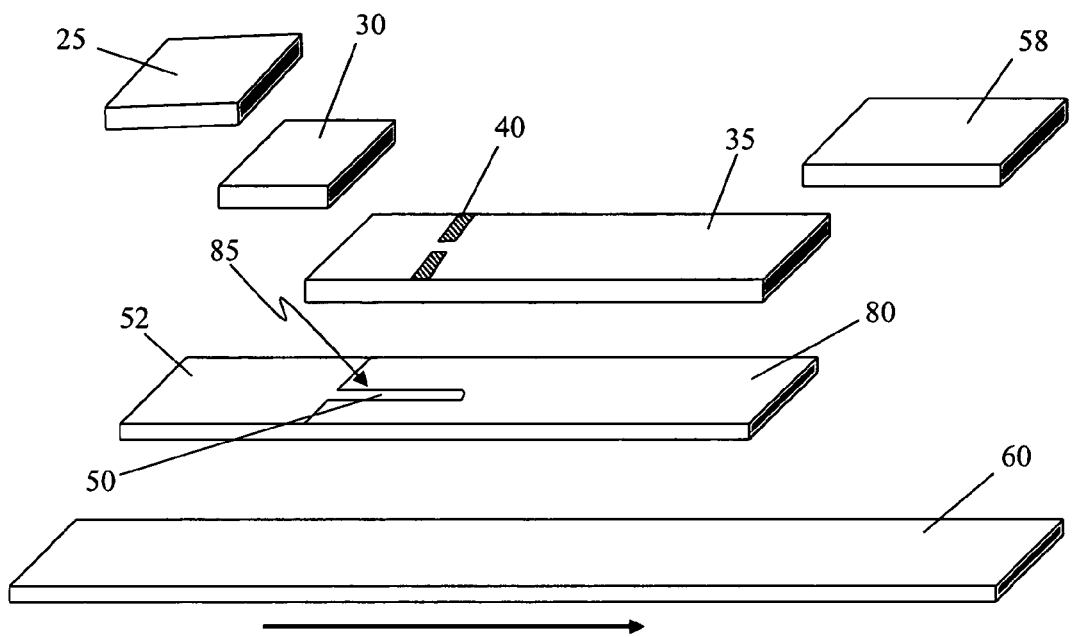
FIG. 3A shows an exploded view of another embodiment of a device of the invention. In this embodiment, the positive control area is demarcated by a filament 50 present below the nitrocellulose. In this embodiment, the filament takes the form of a tongue protruding from a positive control pad 52 and fits into the groove 85 of a support layer 80.
Figure 3B:
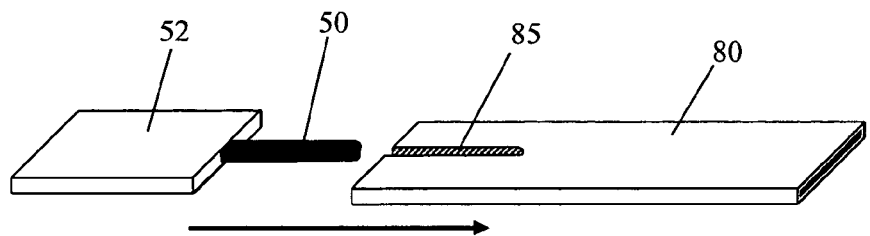
FIG. 3B illustrates the positive control portion of the embodiment shown in FIG. 3A. The filament 50 is a tongue that protrudes from the positive control pad 52. The filament (tinted area) has been treated with one or more components that change from a first color to a second color when wetted. The filament fits into a groove 85 cut into the support layer 80.

With reference to FIGS. 1-3, after application of liquid or liquefied sample to the sample application zone 25, the sample begins to flow through the matrix and down the test strip. The sample enters a reagent zone 30 where reagents for conducting the assay and/or for labeling the analyte react with the sample. The analyte present in the sample is therefore labeled with a detectable label, in this case an antibody for the analyte carrying a gold sol particle. As the sample flows through the device, analyte contained in the fluid sample is labeled with a detectable label and is retained on the analyte binding area of the detection zone. The analyte binding area contains a member of a specific binding pair for a moiety associated with the analyte, in this case an antibody directed to an epitope directly on the analyte. In addition, the color-changing components contained in the positive control filament are wetted as liquid sample flows through the positive control area, and the filament changes from a first color (e.g., white) to a second color (e.g., red).

The positive control filament and the detectable label can be selected to have the same color, so that when labeled analyte binds to the analyte binding area, the interaction of the positive control area and the analyte control area results in the appearance of a recognizable symbol in the detection zone, in this case a "+" sign. In this case, as gold sol accumulates in the analyte binding area, it will produce a red appearance, which interacts with the red positive control filament to produce a "+" sign.

In cases where no analyte is present in the sample, the primary symbol (the minus sign of the positive control area) is apparent in the detection zone, resulting in a minus sign becoming visible after the assay is complete and indicating a negative result for the assay.

Test Kits

A further aspect of the present invention is a kit of the present invention, for determining the presence or absence of an analyte in a fluid, and instructions for use of the device. Test kits of the invention can be packaged in a variety of formats, depending upon the customer's needs.

In one embodiment, the test strips can be configured as "midstream" fertility test devices, having a housing enclosing the test strip, a wick in fluid communication with the sample application zone of the test strip and reagents for detecting a fertility hormone of interests, such as hCG, luteinizing hormone (LH) or follicle stimulating hormone (FSH). The housing has a window aligned with the detection zone, for viewing the test results. In certain embodiments, a kit containing midstream pregnancy devices has one or more individually wrapped devices and one set of instructions. The instructions explain how to perform the test and interpret the test results. For example, a patient provides a urine sample on a sample collection portion of a urine test device, which transmits the urine to a sample application pad on a device of the invention. The fluid passes through the reagent zone and detection zone of the device. If the test is negative (no pregnancy), a minus sign is uncovered when the color-changing component(s) in the positive control area have been wetted by sample, and therefore exhibit the second color. If the test is positive (pregnant), a plus sign is formed when the color changing component(s) in the positive control area interact with the color formed in the analyte binding area.

In various embodiments the kit contain 4 or more ovulation test devices or 6 or more ovulation test devices, one or more pregnancy test device(s), and an instruction booklet explaining use of the devices to identify the time of the LH surge, and how to use the devices to test for pregnancy. The devices can be any described herein. The devices can also be configured as a "cassette" for use in a professional laboratory.

In another embodiment, the kits contain test strips of the present invention. In one embodiment the test strips can be configured for pregnancy testing and packaged in containers having 15 or more test strips or 20 or more test strips, and an instruction insert. This type of kit is convenient for use in professional laboratories performing many pregnancy tests.

Example 1

Construction of hCG Test Device

This example describes the construction of one embodiment of the device of the invention for determining the presence or absence of hCG in a urine sample.

Test strips were constructed according to methods known in the art, except where otherwise noted. Referring to FIG. 6, the positive control area was formed by placement of a positive control filament 50 within a groove 85 that was cut in a support layer 80 to receive the filament. The positive control filament 50 was an extension from a positive control pad 52. In this embodiment the filament and control pad were provided in a double layer, as depicted in FIG. 6. The filament was 0.9 mm×10 mm and made of paper, and was previously treated with 3 µl of water-sensitive ink (purchased from Beijing Chuang-Zin Cheng-Ye Science and Technology Inc. Ltd., Beijing, China under the name "water-sensitive ink"), and dried at room temperature until it was white.

Goat anti-αhCG IgG (4.0 mg/ml) was applied at analyte binding areas on a nitrocellulose strip, which were located at either side of the positive control filament as the device is viewed from above, so that a plus sign would appear to the observer in the event of a positive assay result. The reagent zone contained gold sol labeled mouse anti-βhCG IgG. The portions of the test device were laminated together. Optionally, an anti-human IgG (1.3 mg/ml) can be applied as a second procedural control line at the far end of the nitrocellulose using a microsyringe controlled by a microprocessor.

Example 2

Use of the Devices

After the test strips were constructed, they were tested using hCG positive and negative urine. Three lots of urine were obtained that had been correlated to a positive or negative group as containing an amount of hCG indicative of pregnancy. Lot 1 contained 200 urine samples. Lots 2 and 3 each contained 60 urine samples.

In each case 100% of the urine samples were correctly correlated to their group using the devices and methods of the present invention, for a specificity of greater than 99.9%.

The invention illustratively described herein may be practiced in the absence of any element or elements, limitation or limitations that are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by various embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The invention claimed is:

1. A device for detecting the presence or absence of an analyte in a sample comprising:
    a matrix which defines a flow path for a liquid sample, the matrix having a groove therein;
    a sample application zone on the matrix for receiving the liquid sample;
    a reagent zone on the matrix downstream of the sample application zone and in fluid communication with the sample application zone, the reagent zone comprising a specific binding agent, the specific binding agent comprising a label and a molecule specific for an analyte;
    a detection zone on the matrix downstream of the reagent zone and in fluid communication with the sample application zone and the reagent zone, the detection zone comprising an analyte binding area and a positive control pad, the positive control pad comprising at least one positive control filament that fits within the groove in the matrix, the positive control filament comprising one or more components that exhibit a first color when dry and a second color when wet; and
    wherein in the absence of the analyte, wetting of the positive control pad and the positive control filament causes a first recognizable symbol to form on the matrix, and
    wherein in the presence of the analyte, wetting of the positive control pad, the positive control filament and binding of analyte at the analyte binding area causes a second recognizable symbol to form on the matrix, the second recognizable symbol being different from the first recognizable symbol.

2. The device of claim 1 wherein the first recognizable symbol is in the shape of a minus sign.

3. The device of claim 1 wherein the second recognizable symbol is a plus sign.

4. The device of claim 1 wherein the specific binding agent is an antibody or antibody fragment.

5. The device of claim 1 wherein the specific binding agent binds human chorionic gonadotropin.

6. The device of claim 1 wherein the label comprises a colored particle.

7. The device of claim 6 wherein the colored particle is a dextran bead.

8. The device of claim 1 wherein the analyte binding area comprises a bar situated latitudinally along the axis of the strip.

9. A method of determining the presence or absence of an analyte in a liquid sample comprising:
    placing the liquid sample onto a device comprising:
        a matrix which defines a flow path of a liquid sample, the matrix having a groove therein;
        a sample application zone on the matrix for receiving the liquid sample;
        a reagent zone on the matrix downstream of the sample application zone and in fluid communication with the sample application zone, the reagent zone comprising a specific binding agent, the specific binding agent comprising a label and a molecule specific for an analyte; and
        a detection zone on the matrix downstream of the reagent zone and in fluid communication with the sample application zone and the reagent zone, the detection zone comprising an analyte binding area and a positive control pad, the positive control pad comprising at least one positive control filament that fits within the groove in the matrix, the positive control filament comprising one or more components that exhibit a first color when dry and a second color when wet,
    allowing the liquid sample to flow along the flow path to form a detectable reaction product when analyte is present in the liquid sample; and
    observing the detection zone of the device to determine the presence or absence of analyte in the liquid sample.

10. The method of claim 9 wherein the specific binding agent is an antibody or antibody fragment.

11. The method of claim 10 wherein the first color is white and the second color is red.

12. The method of claim 9 wherein the matrix is a test strip comprised of a bibulous material.

13. A kit comprising:
    a device for determining the presence or absence of an analyte in a fluid comprising:
        a matrix which defines a flow path for a liquid sample, the matrix having a groove therein;
        a sample application zone on the matrix for receiving the liquid sample;
        a reagent zone on the matrix in fluid communication with sample flow from the sample application zone, the reagent zone comprising a specific binding agent, the specific binding agent comprising a label and a molecule specific for an analyte;
        a detection zone on the matrix downstream of the reagent zone and in fluid communication with the sample application zone and the reagent zone, the detection zone comprising an analyte binding area and a positive control pad, the positive control pad comprising at least one positive control filament that fits within the groove in the matrix, the positive control filament comprising one or more components that exhibit a first color when dry and a second color when wet,
    wherein in the absence of the analyte, wetting of the positive control pad and the positive control filament causes a first recognizable symbol to form on the matrix, and
    wherein in the presence of the analyte, wetting of the positive control pad, the positive control filament and binding of analyte at the analyte binding area causes a second recognizable symbol to form on the matrix, the second recognizable symbol being different from the first recognizable symbol; and
    instructions for use of the device.

14. The kit of claim 13 wherein the first recognizable symbol is a minus sign.

15. The kit of claim 13 wherein the second recognizable symbol is a plus sign.

16. The kit of claim 13 wherein the specific binding agent is an antibody or antibody fragment.

17. The kit of claim 13 wherein the specific binding agent is selected from the group consisting of: a specific binding molecule that binds human chorionic gonadotropin and a specific binding molecule that binds luteinizing hormone.

18. The device of claim 1, wherein a first portion of the positive control pad is upstream of the analyte binding area, and wherein a second portion of the positive control pad is downstream of the analyte binding area.

* * * * *